United States Patent [19]

Tam

[11] Patent Number: 5,504,792
[45] Date of Patent: Apr. 2, 1996

[54] METHOD AND SYSTEM FOR MASKING CONE BEAM PROJECTION DATA GENERATED FROM EITHER A REGION OF INTEREST HELICAL SCAN OR A HELICAL SCAN

[75] Inventor: Kwok C. Tam, Schenectady, N.Y.

[73] Assignee: General Electric Company, Schenectady, N.Y.

[21] Appl. No.: 364,349

[22] Filed: Dec. 27, 1994

[51] Int. Cl.$^6$ ..................................................... A61B 6/03
[52] U.S. Cl. ........................................ 378/15; 364/413.15
[58] Field of Search .................. 378/15, 01; 364/413.14, 364/413.15

[56] References Cited

U.S. PATENT DOCUMENTS

| | | | |
|---|---|---|---|
| 5,032,990 | 7/1991 | Eberhard et al. | 364/413.15 |
| 5,187,659 | 2/1993 | Eberhard et al. | 364/413.15 |
| 5,257,183 | 10/1993 | Tam | 364/413.19 |
| 5,390,111 | 2/1995 | Tam | 364/413.14 |
| 5,461,650 | 10/1995 | Tam | 378/4 |

OTHER PUBLICATIONS

"Image Reconstruction from Cone-Beam Projections: Necessary and Sufficient Conditions and Reconstruction Methods" by Bruce D. Smith, IEEE Trans on Medical Imaging, vol. MI-4, No. 1, Mar. 1985, pp. 14–25.
"Three–Dimensional Helical–Scan Computed Tomography Using Cone–Beam Projections", by Hiroyuki Kudo, et al, Systems and Computers in Japan, vol. 23, No. 12, 1992, pp. 75–82.
"Cone–Beam Tomography: Recent Advances and a Tutorial Review", by Bruce D. Smith, Optical Engineering, May 1990, vol. 29, No. 5, pp. 524–534.

*Primary Examiner*—David P. Porta
*Assistant Examiner*—David Vernan Bruce
*Attorney, Agent, or Firm*—David C. Goldman; Paul R. Webb, II

[57] ABSTRACT

The present invention discloses a method and system for performing three-dimensional computerized tomography imaging of a region of interest of an object. In the present invention, a scanning trajectory is provided about the object. The scanning trajectory includes a first scanning circle, a second scanning circle, and a helical scanning path connecting the first scanning circle and the second scanning circle. The scanning trajectory is then sampled with a plurality of cone beam source positions. Cone beam energy is emitted along the scanning trajectory from each of the plurality of cone beam source positions towards a portion of the object. Cone beam energy passing through the object is acquired on a detector as cone beam projection data. The cone beam projection data is then masked with a plurality of masks. Each of the masks remove cone beam projection data that is outside the region of interest of the object and retain cone beam projection data that is within the region of interest of the object. An image of the region of interest of the object is reconstructed from the masked cone beam projection data.

25 Claims, 8 Drawing Sheets

METHOD AND SYSTEM FOR MASKING CONE BEAM PROJECTION DATA GENERATED FROM EITHER A REGION OF INTEREST HELICAL SCAN OR A HELICAL SCAN

BACKGROUND OF THE INVENTION

The present invention relates generally to three-dimensional (3D) computerized tomography (CT) and more particularly to masking cone beam projection data generated from either a region of interest helical scan or a helical scan.

To acquire cone beam projection data in a cone-beam CT implementation, an object is scanned, preferably over a 360° angular range, either by moving a cone beam x-ray source in a scanning circle about the object, while keeping a two-dimensional (2D) array detector fixed with reference to the cone beam x-ray source or by rotating the object while the x-ray source and detector remain stationary. The image of the object is reconstructed by using a Radon inversion process, in which the total Radon transform of the cone beam projection data is computed. The first step in the reconstruction process is to partition the cone beam projection data into a plurality of vertical planes in Radon space. Within each vertical plane, the Radon derivative data is computed. Next, the Radon derivative data is converted to Radon data on a plurality of polar grid points located on each vertical plane. A 3D inverse Radon transformation then converts the Radon data into an image. The image is then reconstructed for display.

A problem with the above-described Radon inversion process is that it is difficult to image an object having rather long, wide, or tall dimensions, because it is hard to procure a detector array having sufficient height or width to obtain the cone beam projection data. Generally, the detector array should have a height and width that is somewhat greater than the height and width of the object or region of interest of the object, otherwise, some x-ray data will be missed. If x-ray data is missed, then it will be very hard to image a region of interest of the object, since the cone beam projection data may not exclusively represent data from such a region of interest. Consequently, the height of the detector array limits the height of the region that can be scanned.

However, it is possible to scan and reconstruct an image of an object with cone beam x-rays, using a detector array that is shorter than the object. In this approach, the x-ray source scans the object along a helix scan path. In order to scan a region of interest of the object, a circular scan at the top level of the region of interest and a circular scan at the bottom level of the region of interest are added to the helical scan. The only height requirement is that the detector array should be longer than the distance between adjacent turns in the helical scan path. In order to reconstruct an image of the region of interest, it is necessary to compute the Radon transform for each plane intersecting the region of interest from the totality of the cone beam projection data. This is achieved by combining the cone beam projection data taken at different source positions on the scan path. Combining the cone beam projection data taken at different source positions on the scan path requires that the angular range of the cone beam projection data for each of the source positions be used to later compute the Radon derivative and that the exact number of source positions that contribute to a particular Radon point be maintained. The reconstruction process for this approach is very complicated and requires a lot of time and effort to perform.

SUMMARY OF THE INVENTION

Therefore, it is a primary objective of the present invention to provide a method and system that greatly simplifies the reconstruction process for imaging an object and a region of interest of the object with a short area detector.

A second object of the present invention is to preprocess the cone beam projection data with masks in order to simplify image reconstruction.

Thus, in accordance with the present invention, there is provided a method for performing three-dimensional computerized tomography imaging of an object. The method comprises providing a scanning trajectory about the object. The scanning trajectory includes a helical scanning path. The scanning trajectory is then sampled with a plurality of cone beam source positions. Cone beam energy is emitted along the scanning trajectory from each of the plurality of cone beam source positions towards the object. Cone beam energy passing through the object is acquired on a detector as cone beam projection data. The cone beam projection data is then masked with a mask. The masked cone beam projection data is then reconstructed and displayed.

In accordance with another embodiment of the present invention, there is provided a method for performing three-dimensional computerized tomography imaging of a region of interest of an object. The method comprises providing a scanning trajectory about the object. The scanning trajectory includes a first scanning circle, a second scanning circle, and a helical scanning path connecting the first scanning circle and the second scanning circle. The scanning trajectory is then sampled with a plurality of cone beam source positions. Cone beam energy is emitted along the scanning trajectory from each of the plurality of cone beam source positions towards a portion of the object. Cone beam energy passing through the object is acquired on a detector as cone beam projection data. The cone beam projection data is then masked with a plurality of masks. Each of the masks remove cone beam projection data that is outside the region of interest of the object and retain cone beam projection data that is within the region of interest of the object. An image of the region of interest of the object is then reconstructed from the masked cone beam projection data.

In accordance with a third embodiment of the present invention, there is provided a system for performing three-dimensional computerized tomography imaging of an object, comprising a cone beam energy source. A scanning means moves the cone beam energy source about an object in a scanning trajectory that includes a helical scanning path. The scanning means emits cone beam energy at the object from a plurality of cone beam source positions along the scanning trajectory. A detector acquires cone beam energy passing through the object as cone beam projection data. A masking means masks the cone beam projection data with a mask. A reconstructing means reconstructs an image of the object from the masked cone beam projection data.

In accordance with another embodiment of the present invention, there is provided a system for performing three-dimensional computerized tomography imaging of a region of interest of an object, comprising a cone beam energy source. A scanning means moves the cone beam energy source about an object in a scanning trajectory that includes a first scanning circle, a second scanning circle, and a helical scanning path connecting the first scanning circle and the second scanning circle. The scanning means emits cone beam energy at the object from a plurality of cone beam source positions along the scanning trajectory. A detector acquires cone beam energy passing through the object as cone beam projection data. A masking means masks the cone beam projection data with a plurality of masks. Each of the masks remove cone beam projection data that is outside the region of interest of the object and retain cone beam projection data that is within the region of interest of the object. A reconstructing means reconstructs an image of the region of interest of the object from the masked cone beam projection data.

While the present invention will hereinafter be described in connection with a preferred embodiment and method of use, it will be understood that it is not intended to limit the invention to this embodiment. Instead, it is intended to cover all alternatives, modifications and equivalents as may be included within the spirit and scope of the present invention as defined by the appended claims.

DETAILED DESCRIPTION OF THE PRESENT INVENTION

Figure 1:
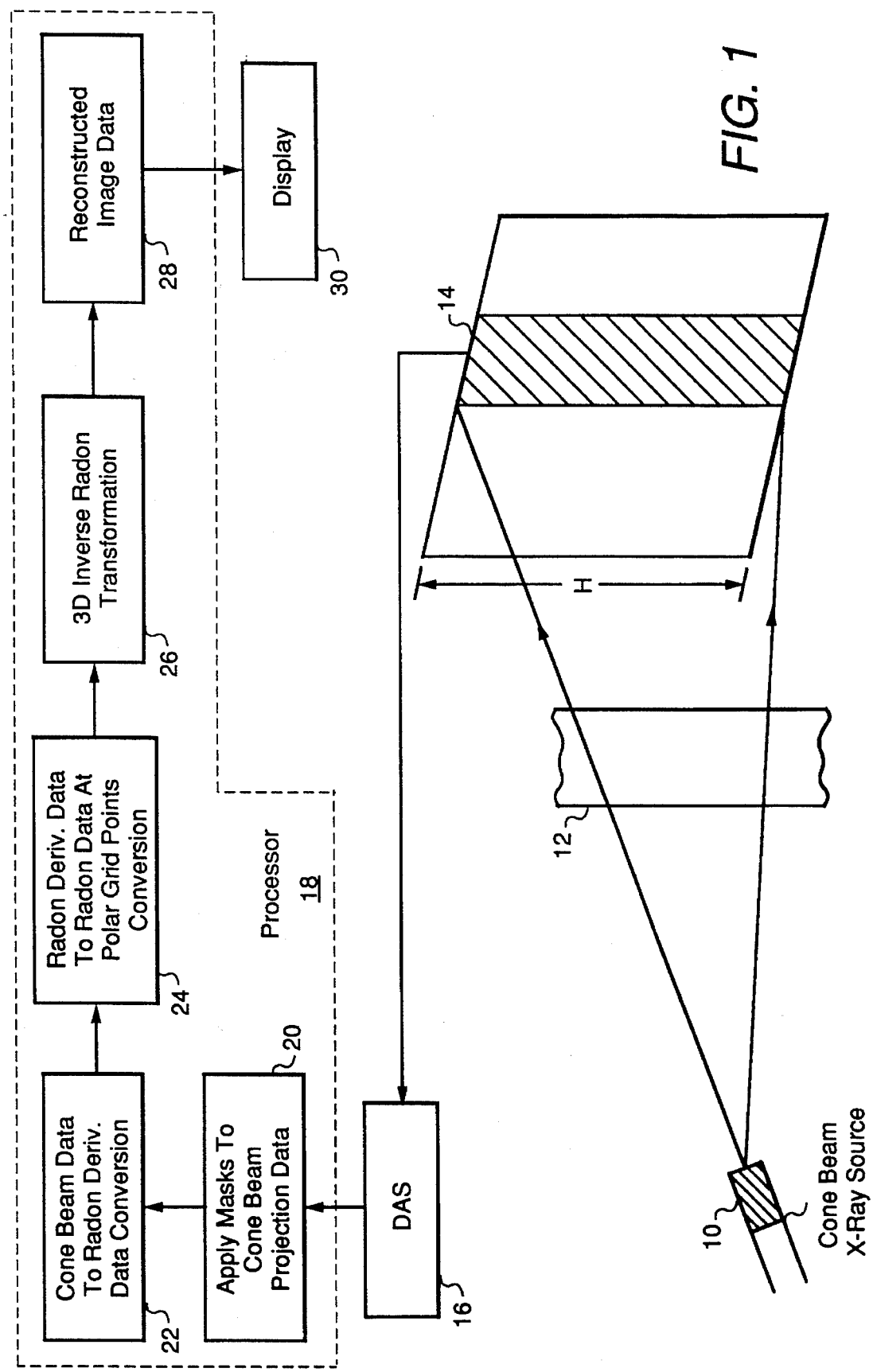
FIG. 1 is a perspective view of a cone beam CT system used in the present invention.

In FIG. 1, cone beam energy is emitted from a cone beam x-ray source 10 and passed through at least a region of interest of an object 12. The cone beam energy passing through the region of interest of the object is detected by a 2D array detector 14 which comprises an array of individual detector elements. Complete information is obtained by moving the cone beam x-ray source 10 and the detector 14 in relation to the object 12. For example, the object can be rotated about a vertical axis with respect to the x-ray source and the detector or the object can remain stationary while the source and detector are rotated about the object. Cone beam energy that penetrates the object is detected by the detector as cone beam projection data. The cone beam projection data is converted to corresponding electrical signals and sent to a data acquisition system 16 which registers the electrical signals. The electrical signals corresponding to the cone beam projection data in the data acquisition system (DAS) are then sent to a processor 18.

The processor performs a series of data conversions that are necessary to reconstruct an image of the object. In particular, a plurality of masks are applied to the cone beam projection data at 20. Each of the masks remove cone beam projection data that is outside the region of interest of the object and retain cone beam projection data that is within the region of interest of the object. The details of the masking operation are described below in further detail. After applying the masks, the masked cone beam projection data is converted to Radon derivative data at 22 using the techniques described in the U.S. Pat. No. 5,257,183, which are incorporated herein by reference. The Radon derivative data is then converted to Radon data at 24 using techniques described in commonly assigned, co-pending, U.S. patent application Ser. No. 08/100,818, which is incorporated herein by reference. The Radon data at the polar grid points is then used to perform an inverse 3D Radon transformation at 26 using the techniques described in detail in commonly assigned U.S. patent application Ser. No. 07/631,818, now abandoned, which is incorporated herein by reference. After the 3D inverse Radon transformation, reconstructed image data is obtained and sent to block 28. The reconstructed image data is then fed from the processor to a display 30, which provides a 3D CT image of the region of interest of the object 12.

Figure 2:
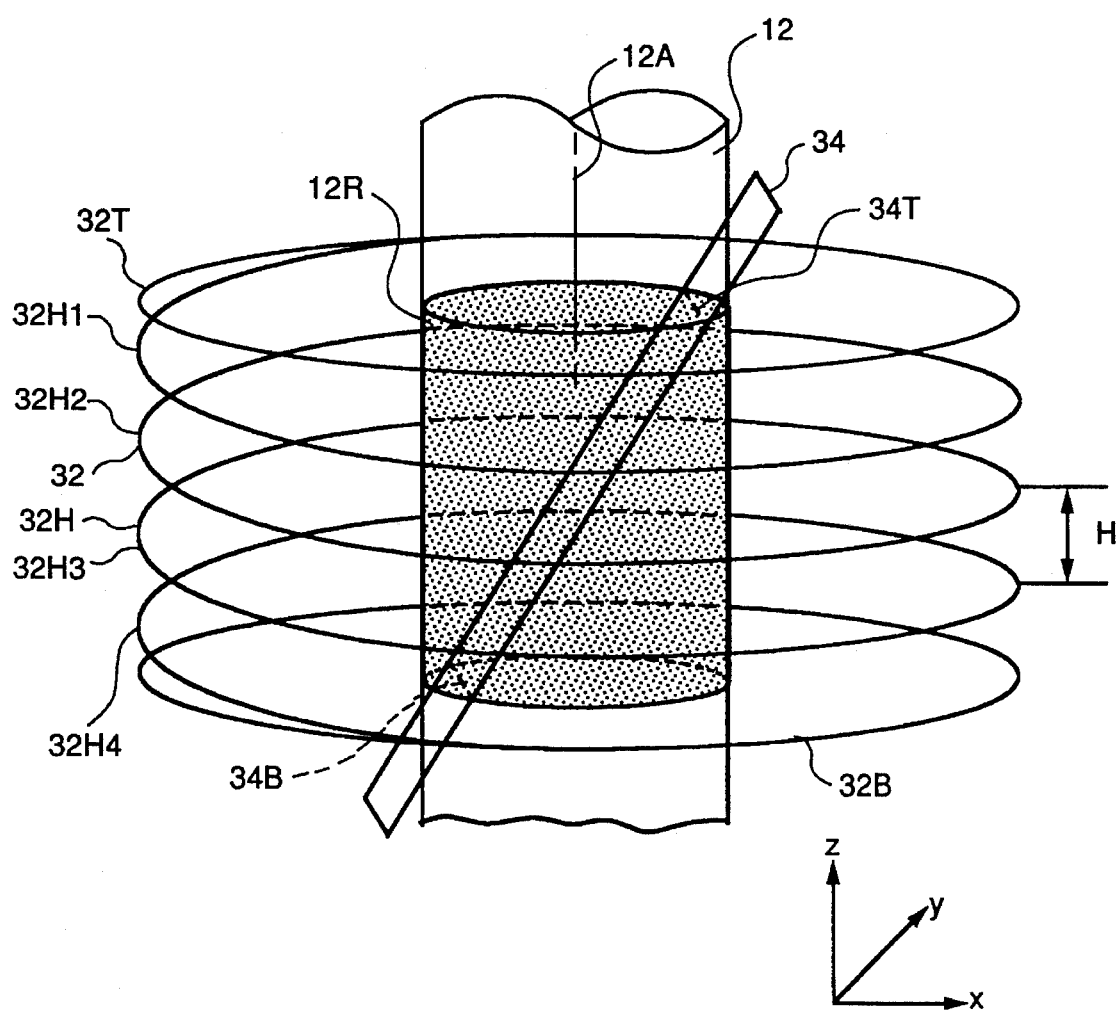
FIG. 2 is a perspective view of a region of interest of an object and a scanning trajectory.

A scanning trajectory 32 for the CT implementation of FIG. 1 is shown in FIG. 2. The scanning trajectory 32 surrounds a region of interest 12R of the object 12 which is less than the total extent of the relatively long or tall object. The scanning trajectory comprises a top circular scan path 32T scanning the top port ion of the region of interest, a bottom circular scan path 32B scanning the bottom portion of the region of interest, and a helical scan path 32H connecting the top circular scan path to the bottom circular scan path. The helical portion 32H has a plurality of stages 32H1, 32H2, 32H3, and 32H4. The stages are mutually spaced by a distance H, which corresponds to the height of the detector 14. This enables the detector 14 to assemble a complete set of cone beam projection data relative to the region of interest 12R without any overlap. This concept is explained in further detail in commonly-assigned, co-pending, U.S. patent application Ser. No. 08/131,180 entitled "THREE DIMENSIONAL COMPUTERIZED TOMOGRAPHY SCANNING METHOD AND SYSTEM FOR IMAGING LARGE OBJECTS WITH SMALLER AREA DETECTORS," filed on Oct. 4, 1993, which is incorporated herein by reference. The top circular scan path 32T, the bottom circular scan path 32B, and the various stages of helical scan path 32H (i.e., 32H1–32H4) collectively define a cylinder centered about an axis 12A through the region of interest 12R. The stages of helical portion 32H refer to each of the turns or revolutions formed by the helical path about axis 12A.

In FIGS. 1 and 2, the scanning trajectory 32 corresponds to the movement of the cone beam x-ray source 10 about the object 12 with the detector 14 being maintained in a fixed position relative to the source. However, instead of scanning the cone beam x-ray source 10 and detector 14 about the object 12 in the scanning trajectory 32 shown in FIG. 2, the object 12 could be rotated and moved to produce the illustrated scan path. In that case, the scan path would illustrate the apparent movement of the source with respect to a frame of reference fixed to the object 12.

In FIG. 2, the object 12 is shown as a relatively long cylinder having a cylindrical region of interest 12R therein. However, it is within the scope of the present invention to use objects having other shapes. In the present invention, the cylinder corresponding to the region of interest 12R will be referred to as the object cylinder. That object cylinder is enclosed within a larger cylinder called the scan path cylinder. The scan path cylinder is defined by the top circular scan path 32T, the bottom circular scan path 32B, and the stages of the helical scan path 32H, which effectively wrap around the imaginary cylindrical surface connecting the two circles.

Figure 3:
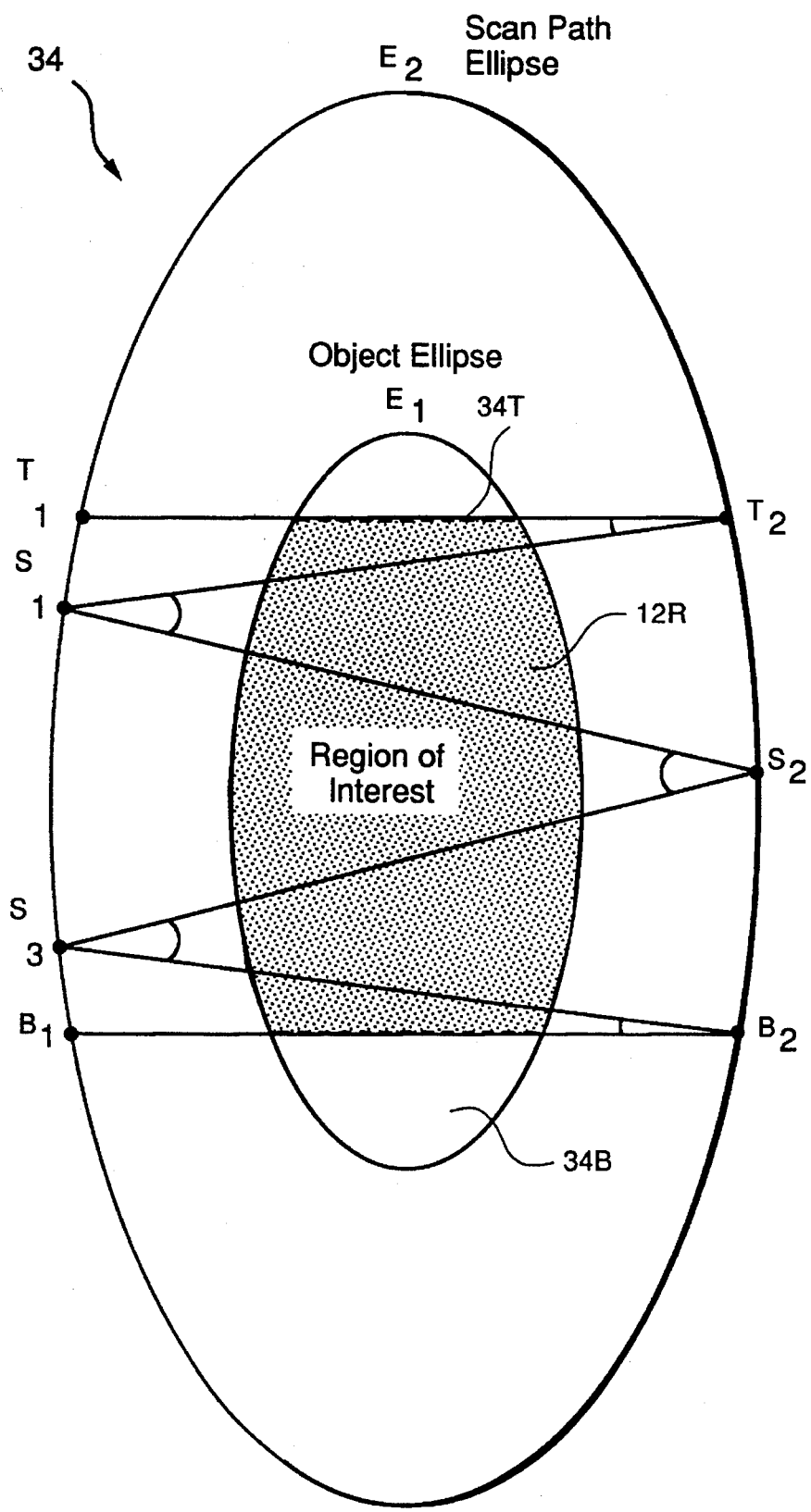
FIG. 3 is a top view taken of a plane in FIG. 2.

In order to reconstruct an image of the region of interest of the object, all planes intersecting the region of interest have to be illuminated by the cone beam energy source so that complete cone beam projection data can be obtained. In FIG. 2, a plane 34 is shown intersecting the region of interest 12R. Since a plane intersects a cylinder in an ellipse, the plane 34 intersects the object cylinder 12 and the scan path cylinder in the form of two ellipses, with one ellipse being inside the other. A view of the object cylinder 12 and the scan path cylinder taken in plane 34 of FIG. 2 is shown in FIG. 3. The intersection between the plane 34 and the object 12 defines an object ellipse $E_1$, whereas the intersection between the plane 34 and the scanning trajectory 32 defines an ellipse $E_2$. The region of interest 12R is the portion of the object ellipse $E_1$ which is between the top circular scan path 32T and the bottom circular scan path 32B and the intersection with the plane 34.

Since the helical scan path 32H lies on the scan path cylinder, the intersections between the helical stages and the plane are points that lie on the ellipse $E_2$. The source positions on the helical scan path are labeled $S_1$, $S_2$, and $S_3$ in FIG. 3 For ease of illustration and discussion, it is assumed that there are only three such source positions, but it will be readily understood that normally a larger number of points of intersection would occur and would be utilized. It should be appreciated that the top circular scan path 32T of FIG. 2 intersects the plane 34 of FIG. 3 in two points $T_1$ and $T_2$ which lie at the intersection between $E_2$ and the top edge of the region of interest 12R. Likewise, the bottom circular scan 32B intersects the plane 34 in the two points $B_1$ and $B_2$ which lie at the intersection between ellipse $E_2$ and the bottom edge of the region of interest 12R.

Figure 4:
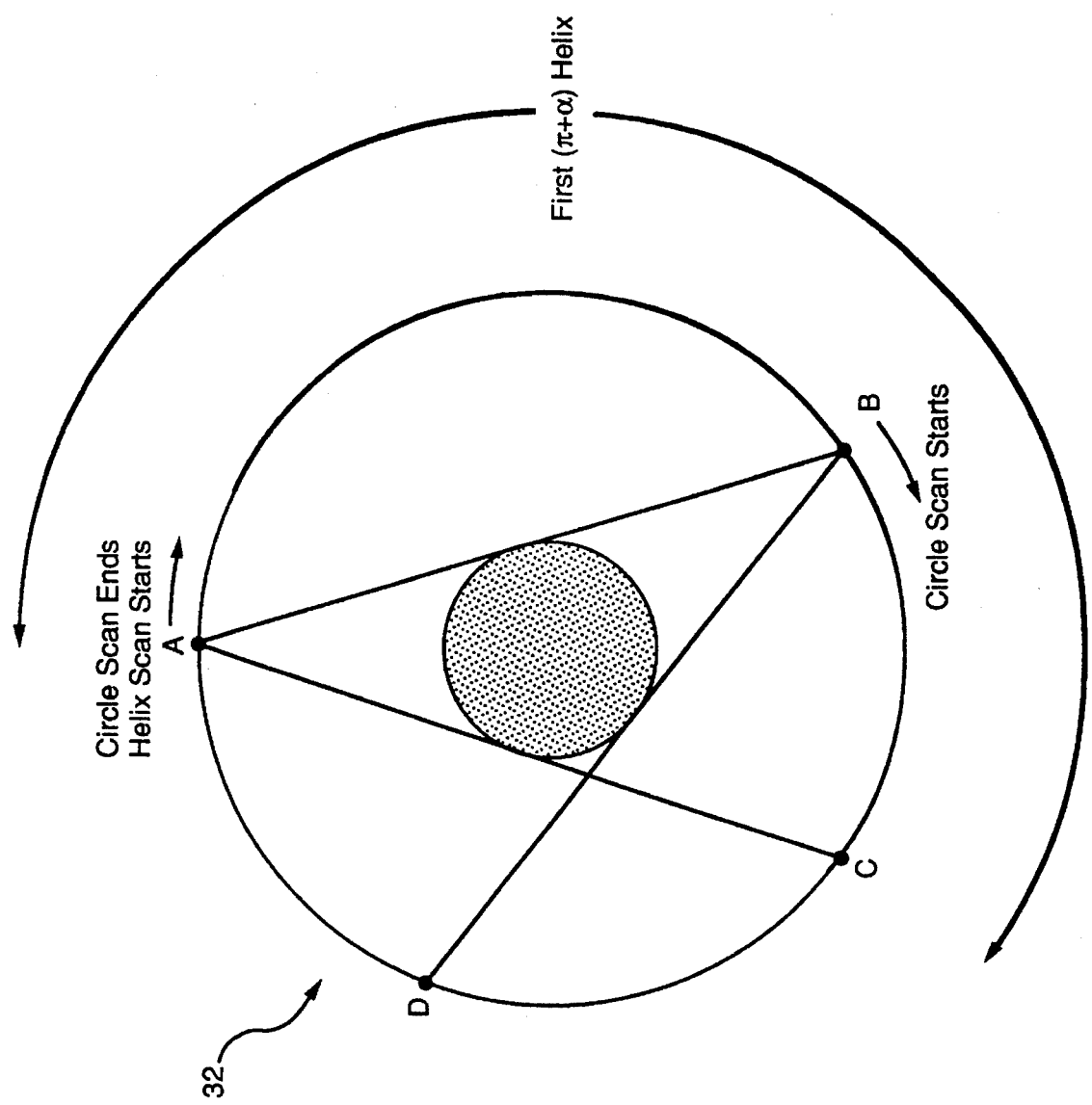
FIG. 4 is a top view of the scanning trajectory about the object.

In order to image the region of interest 12R, the Radon derivative for the portion of the plane 34 that lies within the region of interest needs to computed. As mentioned earlier, this quantity is obtained by acquiring the cone beam projection data generated from the source positions in the region of interest and combining the partial results computed at the various source positions. In FIG. 3, the lines connecting $T_1$ to $T_2$, $T_2$ to $S_1$, $S_1$ to $S_2$, $S_2$ to $S_3$, $S_3$ to $B_2$, and $B_2$ to $B_1$ on the ellipse $E_2$, indicate the beams of x-rays or other imaging energy generated from the source positions on the scanning trajectory. In FIG. 3, the source positions $T_2$, $S_1$, $S_2$, $S_3$, and $B_2$ each contribute to the Radon derivative. Therefore, the Radon derivative for these source position needs to be computed and summed together. So, when the source is at position $T_2$, the detector will be retaining energy relative to the plane of view of FIG. 3, which corresponds to rays of energy bound between $T_1T_2$, and $S_1T_2$. Therefore, the Radon derivative data for the portion of plane 34 bound by $T_1T_2$ and $S_1T_2$ is computed. When the source is at position $S_1$, cone beam data within the angle bound by $T_2S_1$ and $S_2S_1$ is retained and the Radon derivative data for the portion of the plane 34 bound by $T_2S_1$ and $S_2S_1$ is computed. When the source is at position $S_2$, the detector retains data corresponding to that portion of 12R between lines $S_1S_2$ and $S_3S_2$ and computes the Radon derivative data for the portion of the plane 34 bound by $S_1S_2$ and $S_3S_2$. When the source is at position $S_3$, cone beam data corresponding to the angle $S_2S_3$ and $B_2S_3$ is retained and the Radon derivative data for the portion of the plane 34 bound by $S_2S_3$ and $B_2S_3$ is computed. When the source is at position $B_2$, cone beam data corresponding to the angle $S_3B_2$ and $B_1B_2$ is retained and the Radon derivative data for the portion of the plane 34 bound by $S_3B_2$ and $B_1B_2$ is computed. By obtaining the five partial results corresponding to the five source positions $T_2$, $S_1$, $S_2$, $S_3$ and $B_2$, the Radon derivative for all of the illustrated planes corresponding to that portion of region of interest 12R in the plane of view of FIG. 4 is obtained. Further details of this approach are described in commonly-assigned, co-pending U.S. patent application Ser. No. 08/150,318 entitled "HELICAL AND CIRCLE SCAN REGION OF INTEREST COMPUTERIZED TOMOGRAPHY" filed on Nov. 12, 1993, which is incorporated herein by reference.

As mentioned above, combining the cone beam projection data taken at different source positions on the scan path as in U.S. patent application Ser. No. 08/150,318, is a very complicated approach. The present invention has simplified this reconstruction process by applying a plurality of masks to the portion of the plane 34 that lies within the region of interest. By using a plurality of masks, the present invention has eliminated a lot of the above computations. The masks are applied to the cone beam projection data generated from the source positions that are in each plane intersecting with the region of interest. Each of the masks comprise a top curve and a bottom curve. Cone beam projection data that is outside the region bounded by the curves is removed and cone beam projection data that is within the region bounded by the curve is retained for further processing. Since the plane 34 will intersect the detector 14 in the form of a line, it is only necessary to obtain cone beam projection data from the plane that lies between the projection of the scanning trajectory. The shape of each mask depends on the location of the source in the scan path. Thus, it is necessary to divide the scanning trajectory 32 into five regions as illustrated in FIG. 4. In particular, five regions occur at the last ($\pi+\alpha$) turn of the top circular scan path 32T, the first ($\pi+\alpha$) turn of the helical scan path 32H, the interior portion of the helical scan path 32H (i.e., after the first ($\pi+\alpha$) turn and before the last ($\pi+\alpha$) turn), the last ($\pi+\alpha$) turn of the helical scan path 32H, and first ($\pi+\alpha$) turn of the bottom circular scan path 32B.

Figure 5:
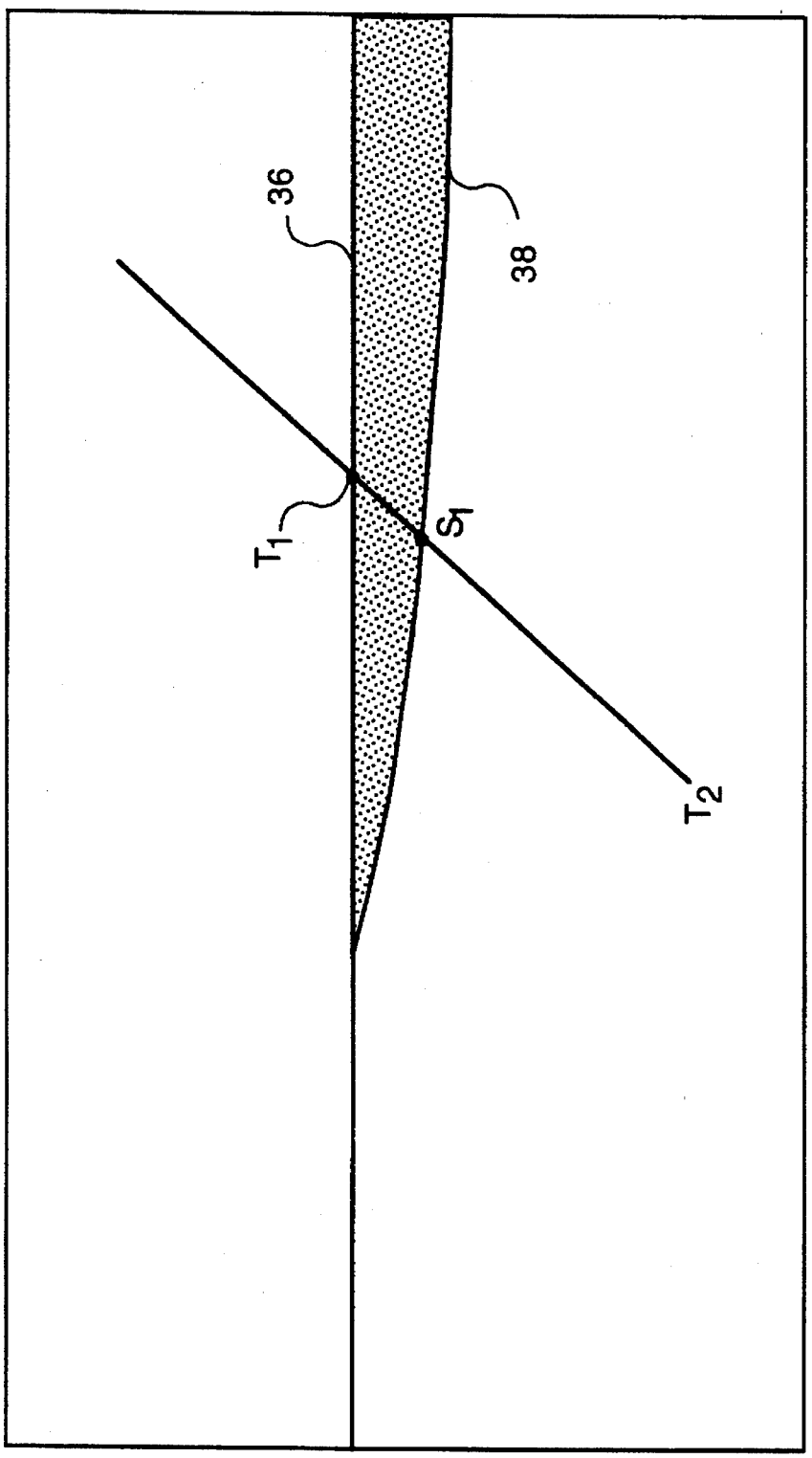
FIG. 5 shows the geometry of a mask that is applied to cone beam projection generated at the ($\pi+\alpha$) turn of the top circular scan path of the scanning trajectory.
Figure 6:
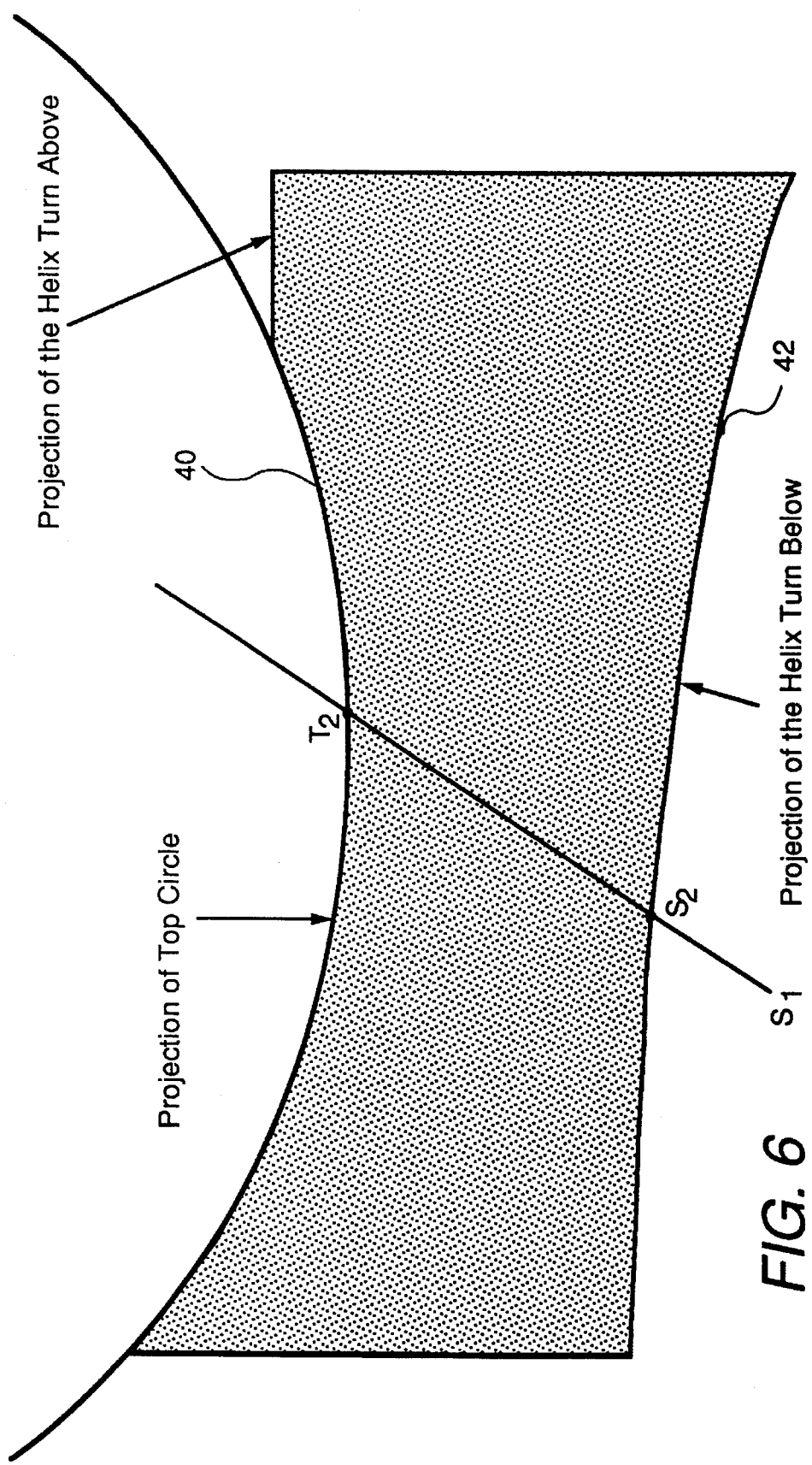
FIG. 6 shows the geometry of a mask that is applied to cone beam projection generated at the ($\pi+\alpha$) turn of the helical scan path of the scanning trajectory.
Figure 7:
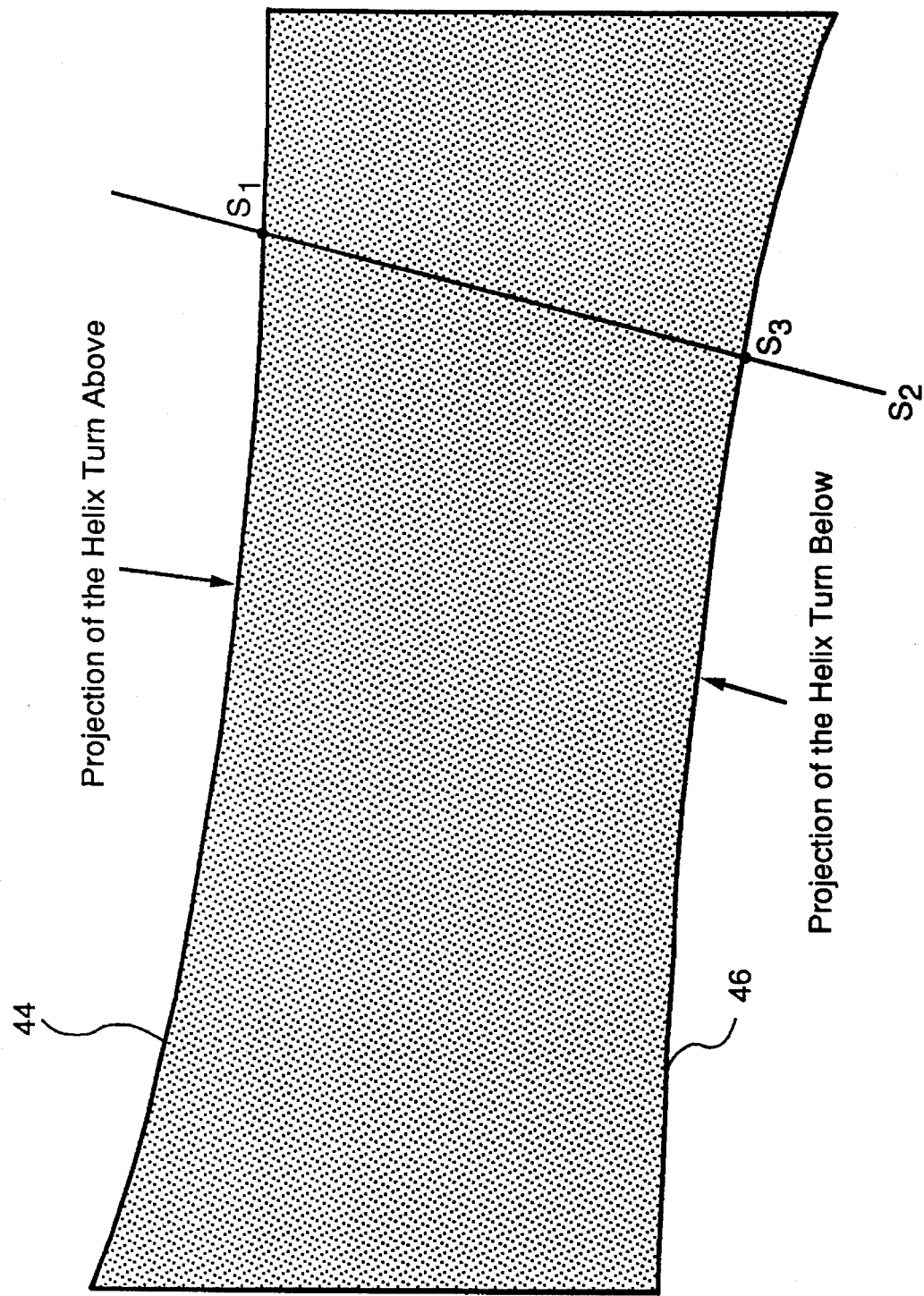
FIG. 7 shows the geometry of a mask that is applied to cone beam projection generated at the interior portion of the helical scan path of the scanning trajectory.

The geometry for the masks occurring at each of these locations is illustrated in FIGS. 5–7. In the present invention, it is assumed that the helical scan path rotates from top to bottom in a clockwise direction. FIG. 5 shows the geometry of the mask that is applied at the ($\pi+\alpha$) turn of the top circular scan path 32T. This point corresponds to the view from the source position $T_2$ towards $T_1$ and $S_1$ in FIG. 3. At this point, $T_1$ is on the top circular scan path and will project onto the detector as a straight line 36, while $S_1$ is on the helical scan path and will project onto the detector as a curve 38. The curve 38 is defined by the following equation:

$$y = -\frac{h}{2\pi}\left[\pi + \tan^{-1}\left(\frac{a}{x}\right)\right]\left(1 + \frac{x^2}{a^2}\right) \quad x \geq 0 \quad (1)$$

$$y = -\frac{h}{2\pi}\tan^{-1}\left(\frac{a}{x}\right)\left(1 + \frac{x^2}{a^2}\right) \quad x < 0,$$

wherein a is the radius of the helix and h is the distance between adjacent helix turns. FIG. 5 gives the general shape of the mask. The exact shape of the mask is obtained by moving the mask in FIG. 5 to the left or to the right depending on the exact location of the source position in the top circular scan path. The cone beam projection data that is bounded between the top curve 36 and the bottom curve 38 is retained, while the cone beam projection data outside the top curve and the bottom curve is removed.

FIG. 6 shows the geometry of the mask that is applied at the first ($\pi+\alpha$) turn of the helical scan path 32H. This point corresponds to the view from the source position $S_1$ towards $T_2$ and $S_2$ in FIG. 3. At this point, $T_2$ is on the circular scan path and will project onto the detector from $S_1$ as a curve 40, while $S_2$ is on the helical scan path and will project onto the detector as a curve 42. The curve 40 is the intersection of two curves, the first curve being the top curve of the interior helix mask defined by the following equation:

$$y = \frac{h}{2\pi} \tan^{-1}\left(\frac{a}{x}\right)\left(1 + \frac{x^2}{a^2}\right) \quad x \geq 0 \quad (2)$$

$$y = \frac{h}{2\pi}\left[\pi + \tan^{-1}\left(\frac{a}{x}\right)\right]\left(1 + \frac{x^2}{a^2}\right) \quad x < 0,$$

wherein a is the radius of the helix and h is the distance between adjacent helix turns, and the second curve is the cone beam projection of the top circular scan path projected from the source defined by the following equation:

$$y = b\left(1 + \frac{x^2}{a^2}\right) \quad (3)$$

wherein a is the radius of the circle and 2b is the distance between the top and bottom circular scan paths. The bottom curve 42 is the bottom curve of the interior helix mask and is defined by equation 1. FIG. 6 gives the general shape of the mask. The exact shape of the mask is obtained by moving the mask in FIG. 6 to the left or to the right depending on the exact location of the source position in the helical scan path. The cone beam projection data that is bounded between the top curve 40 and the bottom curve 42 is retained, while the cone beam projection data outside the top curve and the bottom curve is removed.

FIG. 7 shows the geometry of the mask that is applied at the interior portion of the helix (i.e., after the first $(\pi+\alpha)$ turn and before the last $(\pi+\alpha)$ turn of the helical scan path 32H. This point corresponds to the view from the source position $S_2$ towards $S_1$ and $S_3$ in FIG. 3. At this point, both $S_1$ and $S_3$ are on the helical scan path and will project onto the detector as a curve 44 and 46. The curve 44 is defined by equation 2, while the curve 46 is defined by equation 1. The cone beam projection data that is bounded between the top curve 44 and the bottom curve 46 is retained, while the cone beam projection data outside the top curve and the bottom curve is removed.

The geometry of the mask that is applied at the last turn of the helical scan path is very similar to the mask shown in FIG. 6, except that it is rotated 180°, because at this point, the view is from the source position $S_3$ towards $S_2$ and $B_2$. This mask will have a top curve defined by equation 2 while the bottom curve is the intersection of two curves, the bottom curve of the interior helix defined by equation 1, and the cone beam projection of the bottom circular scan path projected from the source defined by the following equation:

$$y = -b\left(1 + \frac{x^2}{a^2}\right) \quad (4)$$

wherein a is the radius of the circle and 2b is the distance between the top and bottom circular scan paths. The exact shape of the mask is obtained by moving the mask to the left or to the right depending on the exact location of the source position in the helical scan path. The cone beam projection data that is bounded between the top curve and the bottom curve is retained, while the cone beam projection data outside the top curve and the bottom curve is removed.

The geometry of the mask that is applied at the first $(\pi+\alpha)$ turn of the bottom circular scan path is very similar to the mask shown in FIG. 5, except that it is rotated 180°, because at this point, the view is from the source position $B_2$ towards $S_3$ and $B_1$. The general shape of this mask will have a top curve defined by equation 2 while the bottom curve is a straight line, since the bottom circular scan path projects as a line. The exact shape of the mask is obtained by moving this general shape to the left or to the right depending on the exact location of the source position in the bottom circular scan path. The cone beam projection data that is bounded between the top curve and the bottom curve is retained, while the cone beam projection data outside the top curve and the bottom curve is removed.

After applying the masks, the cone beam projection data is converted to Radon derivative data at 22. The Radon derivative data is then converted to Radon data at 24. The Radon data at the polar grid points is then used to perform an inverse 3D Radon transformation at 26. After the 3D inverse Radon transformation, reconstructed image data is obtained and sent to block 28. The reconstructed image data is then fed from the processor to a display 30, which provides a 3D CT image of the region of interest of the object.

Figure 8:
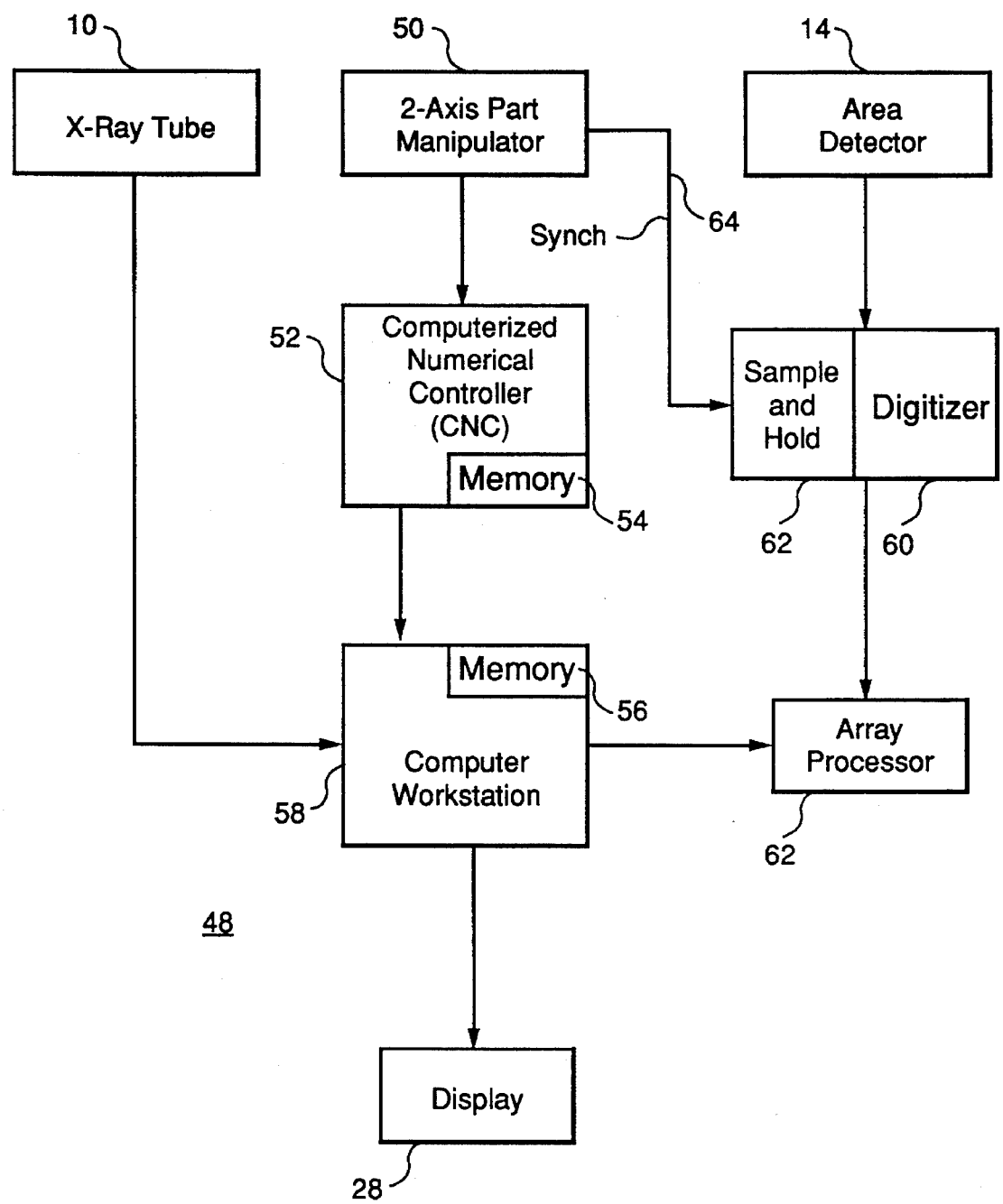
FIG. 8 is a block diagram of the CT system used in the present invention.

A system 48 for performing the above described approach is shown in FIG. 8. The system includes the source 10 and area detector 14. Although the source 10 has been shown as an x-ray tube, the cone beam source 10 could alternately provide neutrons, positrons, or other forms of radiation or electron magnetic energy from a point source. Alternately, other forms of imaging energy might be used. A manipulator 50, which may be a two-axis part manipulator, is used to provide the relative scanning movement between the object and the source 10. Although the manipulator 50 is designed to move the object, the manipulator might alternately move the source 10. The manipulator 50 is controlled by a known computerized numerical controller 52, which may, for example, be of a type made by Aerotech. The controller 52 may include a memory 54 having data defining various scan paths in known fashion. Also, a memory 56 of a computer work station 58, which is connected to the controller 52, may have the data which defines movements of the manipulator 50 and therefore defines the scan path or trajectory. In either case, the defined scan paths would be the two parallel circles with helical turns interconnecting them as discussed in detail above. The computer work station 58 (which may include the processor 18 of FIG. 1) may be a work station made by Sun, although other computer work stations and possibly even personal computers might be used in place of the work station. The computer work station controls the other components of the system 48 in known fashion.

Connected to the area detector 14 is a digitizer 60 which operates in known fashion to convert analog signals from the area detector into digital signals representative of the image of the object under test. The digitizer 60 may include sample and hold circuits 62 operating in response to a synch signal on line 64 in known fashion. The digitized values corresponding to the sense radiation from the detector elements within the detector 14 are supplied from the digitizer 60 to a data array processor 62. The array processor 62, which may be of a known commercially available type such as a Meiko M40, provides the necessary signal processing for the signals coming from the digitizer 60. The array processor 62 (which may include or be the processor 18 of FIG. 1) may perform the necessary image reconstruction and processing such that a display might be connected directly to the array processor to display the images from the CT scan. However, in the present invention, the image data from the array processor 62 is supplied to the computer work station 58 and the computer work station supplies the data, with or without further processing, to the display 28 which displays the CT images. The computer 58 or, more preferably, the array processor 62 then reconstructs an image from the projection data.

It is therefore apparent that there has been provided in accordance with the present invention, a method and system for masking cone beam projection data generated from a region of interest helical scan that fully satisfy the aims and advantages and objectives hereinbefore set forth. The invention has been described with reference to several embodiments, however, it will be appreciated that variations and modifications can be effected by a person of ordinary skill in the art without departing from the scope of the invention. For example, the above described approach could be used to image the object and not just a region of interest of the object. In this embodiment, the scanning trajectory would comprise only the helical scan path about the object and not the top and bottom circular scan paths. Also, since the helical scan path is the only scan path in the scanning trajectory, only one mask is used. The geometry of the mask will have the shape disclosed in FIG. 7. After the mask has been applied, the cone beam projection data is converted to Radon derivative data. The Radon derivative data is then converted to Radon data. The Radon data at the polar grid points is then used to perform an inverse 3D Radon transformation. After the 3D inverse Radon transformation, reconstructed image data is obtained and then fed from the processor to a display, which provides a 3D CT image of the region of interest of the object.

I claim:

1. A method for performing three-dimensional computerized tomography imaging of an object, the method comprising the steps of:

providing a scanning trajectory about the object, the scanning trajectory comprising a helical scanning path;

sampling the scanning trajectory with a plurality of cone beam source positions;

emitting cone beam energy along the scanning trajectory from each of the plurality of cone beam source positions towards the object;

acquiring cone beam energy passing through the object on a detector, the cone beam energy acquired on the detector is cone beam projection data;

masking the cone beam projection data with a mask; and reconstructing an image of the object from the masked cone beam projection data.

2. The method according to claim 1, wherein the mask comprises a top curve and a bottom curve with the cone beam projection data bounded between the top curve and the bottom curve being retained, while the cone beam projection data outside the top curve and the bottom curve being removed.

3. The method according to claim 2, wherein the top and bottom curves are formed from projections of the helical scanning path.

4. A method for performing three-dimensional computerized tomography imaging of a region of interest of an object, the method comprising the steps of:

providing a scanning trajectory about the object, the scanning trajectory comprising a first scanning circle, a second scanning circle, and a helical scanning path connecting the first scanning circle and the second scanning circle;

sampling the scanning trajectory with a plurality of cone beam source positions;

emitting cone beam energy along the scanning trajectory from each of the plurality of cone beam source positions towards a portion of the object;

acquiring cone beam energy passing through the object on a detector, the cone beam energy acquired on the detector is cone beam projection data;

masking the cone beam projection data with a plurality of masks, each of the masks removing cone beam projection data that is outside the region of interest of the object and retaining cone beam projection data that is within the region of interest of the object; and reconstructing an image of the region of interest of the object from the masked cone beam projection data.

5. The method according to claim 4, wherein each of the plurality of masks comprise a top curve and a bottom curve with the cone beam projection data bounded between the top curve and the bottom curve being retained, while the cone beam projection data outside the top curve and the bottom curve being removed.

6. The method according to claim 4, wherein a mask is applied to the cone beam projection data obtained along a last $(\pi+\alpha)$ turn of the first scanning circle, wherein $\alpha$ is a half fan angle of the emitted cone beam energy.

7. The method according to claim 6, wherein the mask comprises a top curve and a bottom curve with the cone beam projection data bounded between the top curve and the bottom curve being retained, while the cone beam projection data outside the top curve and the bottom curve being removed.

8. The method according to claim 7, wherein the top curve is a horizontal line formed from a projection of the first scanning circle and the bottom curve is formed from a projection of the helical scanning path.

9. The method according to claim 4, wherein a mask is applied to the cone beam projection data obtained along a first $(\pi+\alpha)$ turn of the helical scanning path, wherein $\alpha$ is a half fan angle of the emitted cone beam energy.

10. The method according to claim 9, wherein the mask comprises a top curve and a bottom curve with the cone beam projection data bounded between the top curve and the bottom curve being retained, while the cone beam projection data outside the top curve and the bottom curve being removed.

11. The method according to claim 10, wherein the top curve is formed from an intersection of a projection of the first scanning circle and a projection of the helical scanning path and the bottom curve is formed from a projection of the helical scanning path.

12. The method according to claim 4, wherein a mask is applied to the cone beam projection data obtained after a first $(\pi+\alpha)$ turn of the helical scanning path and before a last $(\pi+\alpha)$ turn of the helical scanning path, wherein $\alpha$ is a half fan angle of the emitted cone beam energy.

13. The method according to claim 12, wherein the mask comprises a top curve and a bottom curve with the cone beam projection data bounded between the top curve and the bottom curve being retained, while the cone beam projection data outside the top curve and the bottom curve being removed.

14. The method according to claim 13, wherein the top and bottom curves are formed from projections of the helical scanning path.

15. The method according to claim 4, wherein a mask is applied to the cone beam projection data obtained after a last $(\pi+\alpha)$ turn of the helical scanning path, wherein $\alpha$ is a half fan angle of the emitted cone beam energy.

16. The method according to claim 15, wherein the mask comprises a top curve and a bottom curve with the cone beam projection data bounded between the top curve and the bottom curve being retained, while the cone beam projection data outside the top curve and the bottom curve being removed.

17. The method according to claim 16, wherein the top curve is formed from a projection of the helical scanning path and the bottom curve is formed from an intersection of a projection of the second scanning circle and a projection of the helical scanning path.

18. The method according to claim 4, wherein a mask is applied to the cone beam projection data obtained along a first $(\pi+\alpha)$ turn of the second scanning circle, wherein $\alpha$ is a half fan angle of the emitted cone beam energy.

19. The method according to claim 18, wherein the mask comprises a top curve and a bottom curve with the cone beam projection data bounded between the top curve and the bottom curve being retained, while the cone beam projection data outside the top curve and the bottom curve being removed.

20. The method according to claim 19, wherein the top curve is formed from a projection of the helical scanning path and the bottom curve is a horizontal line formed from a projection of the second scanning circle.

21. A system for performing three-dimensional computerized tomography imaging of an object, comprising:

a cone beam energy source;

scanning means for moving the cone beam energy source about an object in a scanning trajectory comprising a helical scanning path, the scanning means emitting cone beam energy at the object from a plurality of cone beam source positions along the scanning trajectory;

a detector for acquiring cone beam energy passing through the object, the cone beam energy acquired on the detector is cone beam projection data;

means for masking the cone beam projection data with a mask; and means for reconstructing an image of the object from the masked cone beam projection data.

22. A system for performing three-dimensional computerized tomography imaging of a region of interest of an object, comprising:

a cone beam energy source;

scanning means for moving the cone beam energy source about an object in a scanning trajectory comprising a first scanning circle, a second scanning circle, and a helical scanning path connecting the first scanning circle and the second scanning circle, the scanning means emitting cone beam energy at the object from a plurality of cone beam source positions along the scanning trajectory;

a detector for acquiring cone beam energy passing through the object, the cone beam energy acquired on the detector is cone beam projection data;

means for masking the cone beam projection data with a plurality of masks, each of the masks removing cone beam projection data that is outside the region of interest of the object and retaining cone beam projection data that is within the region of interest of the object; and means for reconstructing an image of the region of interest of the object from the masked cone beam projection data.

23. The system according to claim 22, wherein each of the plurality of masks comprise a top curve and a bottom curve with the cone beam projection data bounded between the top curve and the bottom curve being retained, while the cone beam projection data outside the top curve and the bottom curve being removed.

24. The system according to claim 22, further comprising a display coupled to the reconstruction means for displaying an image of the region of interest of the object.

25. The system according to claim 22, wherein the masking means and the reconstructing means comprise a processor.

* * * * *